United States Patent
Fortin et al.

(10) Patent No.: US 9,005,213 B2
(45) Date of Patent: Apr. 14, 2015

(54) CONTROLLED FORCE SURGICAL IMPLANT IMPACTION INSTRUMENT

(71) Applicant: DePuy Synthes Products, LLC, Raynham, MA (US)

(72) Inventors: Michael J. Fortin, Acushnet, MA (US); John W. Cuneo, Norton, MA (US); Rod G. Cameron, Jr., Franklin, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 134 days.

(21) Appl. No.: 13/679,707

(22) Filed: Nov. 16, 2012

(65) Prior Publication Data

US 2014/0142583 A1     May 22, 2014

(51) Int. Cl.
| | |
|---|---|
| A61B 17/58 | (2006.01) |
| A61B 17/60 | (2006.01) |
| A61F 2/00 | (2006.01) |
| A61F 2/46 | (2006.01) |
| A61B 17/16 | (2006.01) |
| A61B 17/92 | (2006.01) |
| A61F 2/34 | (2006.01) |
| A61F 2/30 | (2006.01) |

(52) U.S. Cl.
CPC ........... *A61F 2/4609* (2013.01); *A61B 17/1604* (2013.01); *A61B 17/92* (2013.01); *A61F 2/4637* (2013.01); *A61B 2017/925* (2013.01); *A61B 2017/927* (2013.01); *A61F 2/34* (2013.01); *A61F 2002/30565* (2013.01); *A61F 2002/4641* (2013.01); *A61F 2002/4681* (2013.01)

(58) Field of Classification Search
USPC .......... 606/99, 100, 127–128, 184–185, 182; 81/463; 173/202, 203; 30/367; 225/93
See application file for complete search history.

(56) References Cited

U.S. PATENT DOCUMENTS

| | | | |
|---|---|---|---|
| 2,421,354 A | 5/1947 | Reiter | |
| 5,591,188 A * | 1/1997 | Waisman | ...................... 606/182 |
| 6,132,469 A | 10/2000 | Schroeder | |
| 7,294,150 B1 | 11/2007 | Mandell et al. | |
| 7,708,739 B2 | 5/2010 | Kilburn et al. | |
| 7,927,376 B2 | 4/2011 | Leisinger et al. | |
| 2006/0069395 A1 | 3/2006 | Lebet | |
| 2009/0118741 A1 | 5/2009 | Lebet | |

FOREIGN PATENT DOCUMENTS

| | | |
|---|---|---|
| DE | 195 09 966 A1 | 9/1996 |
| EP | 2 502 580 A1 | 9/2012 |

OTHER PUBLICATIONS

European Search Report corresponding to European Application No. EP 13190734.7, mailed Feb. 28, 2014 (6 pages).

* cited by examiner

*Primary Examiner* — Andrew Yang
(74) *Attorney, Agent, or Firm* — Maginot, Moore & Beck, LLP (57) ABSTRACT

A controlled force surgical implant impaction instrument is provided which includes a striking assembly, a retaining pin, and an actuator component. The striking assembly is configured to impact a surgical implant. The retaining pin is moveable between a first position and a second position. In the first position, the retaining pin inhibits distal movement of the striking assembly. In the second position, the retaining pin does not inhibit distal movement of the striking assembly. The actuator component includes a reloading channel. The actuator component is movable between a third position and a fourth position. In the third position, the retaining pin is in the first position and the retaining pin cannot be forced along the reloading channel. In the fourth position, the striking assembly can be used to move the retaining pin along the reloading channel.

20 Claims, 8 Drawing Sheets

CONTROLLED FORCE SURGICAL IMPLANT IMPACTION INSTRUMENT

BACKGROUND

The hip joint includes an acetabulum and a femur which fit together in such a way that enables rotation at the joint. In particular, the head of the femur fits within the acetabulum to form the "ball in socket" joint at the hip. In total hip arthroplasty, both the acetabular side and the femoral side of the hip joint are replaced with prosthetic devices. The prosthetic device used on the acetabular side includes a cup constructed of a ceramic or an alloy including, for example, titanium and/or cobalt-chromium. The prosthetic device used on the acetabular side also includes a cup liner affixed to the concave surface of the cup in a substantially concentric configuration. The liner is provided to reduce friction between the acetabular cup and the head or "ball" of the femoral prosthesis and to improve retention of the head within the cup.

Liners are constructed from a polymer such as, for example, ultra-high-molecular-weight-polyethylene (UHMWPE) or from a metal or an alloy. Materials are chosen to balance wear resistance and fatigue fracture during use within the patient's body. In use, liners have inherent potential for failure in a variety of ways. First of all, the pressures and forces applied to the prosthesis within the hip joint can cause a liner to crack or fracture due to the material properties of the liner. Secondly, if a liner is improperly sterilized prior to implantation, the patient's hip can become infected. Thirdly, a liner can be seated poorly during placement within the implanted cup which can later cause the liner to dislocate or slip out of position during use. Fourthly, a liner can include a manufacturing flaw causing the surface of the liner to be too rough. In this instance, rather than passing smoothly over the surface of the head of the femoral prosthesis, the liner will then adhere to the surface and wear due to the increased adhesive contact. After bearing weight repeatedly on the adhered surface, particles of the liner can break off the liner and be released into the patient's body causing more surface damage to the liner or causing infection. Finally, once a portion of the liner begins to wear, the liner can become delaminated, exacerbating the wear.

Once a liner fails, it is removed from the patient to prevent further trauma and is replaced with a functioning liner to restore functionality. Removing and replacing part of a hip prosthesis is called hip revision arthroplasty. For the purposes of surgical procedures, such as a hip revision arthroplasty, positions and directions relative to surgical instruments may be described using anatomical directions with reference to the physician using the instrument. Accordingly, as used herein, proximal refers to the longitudinal direction of the instrument toward the user/physician when the instrument is in use and distal refers to the longitudinal direction of the instrument away from the user/physician when the instrument is in use. Additionally, inward refers to the direction of the instrument toward the longitudinal axis of the instrument and outward refers to the direction of the instrument away from the longitudinal axis of the instrument.

When performing surgical procedures such as hip revision arthroplasty, physicians generally attempt to damage as little tissue as possible to minimize further trauma to the patient reducing time and effort required for the patient's recovery. Accordingly, if only the liner of the hip prosthesis requires replacement, it is undesirable to remove the cup as well. To facilitate this goal, surgical procedures and instrumentation have been developed which enable separation and removal of the liner from the acetabular cup during hip revision arthroplasty.

Some acetabular prostheses include a locking mechanism to retain the liner within the cup. Removing liners from such prostheses requires using company and/or device specific removal instruments to disengage the locking mechanism. Using company and/or device specific removal instruments increases the number of specific parts and instruments required for the procedure, thus increasing instrumentation costs. Additionally, using company and/or device specific removal instruments increases the time and precision necessary for the procedure due to accurate alignment of particular elements and performance of particular methods to disengage particular features.

In acetabular prostheses that do not include locking mechanisms, liners can be removed by levering out the liners from the acetabular cups with osteotomes. Osteotomes are sharp cutting and chiseling tools used to cut and separate bones. To remove liners using osteotomes, sharp points of the osteotomes are inserted between the cups and the liners. The osteotomes are then levered against the cups to pop the liners out. Using osteotomes to remove liners increases the time and precision necessary for the procedure due to precise placement and manipulation of sharp cutting tools. Additionally, using osteotomes to remove liners employs blunt force and tools which are not necessarily specially adapted to the goal, introducing risks for error. For example, using osteotomes to remove liners potentially results in inadvertent cutting or slicing off parts of the liners which are then loose in the surgical environment.

Another way to remove liners from acetabular prostheses that do not include locking mechanisms is to drill a hole in the liner with a cortical screw and subsequently insert a cancellous screw having a larger diameter than the cortical screw into the drilled hole. The cancellous screw engages the liner along the sides of the drilled hole and the liner is then pulled apart from the acetabular cup by pulling outwardly on the cancellous screw. Using cortical and cancellous screws to remove liners increases the time and precision necessary for the procedure due to precise placement and manipulation of the screws and the drill. Additionally, using cortical and cancellous screws to remove liners employs and tools which are not necessarily specially adapted to the goal, introducing risks for error. For example, using cortical and cancellous screws to remove liners potentially results in drilling the holes into the liners at unfavorable angles which then requires more time to drill a new hole and/or further damages the prosthesis.

Given the above discussion, it would be advantageous to provide an improved acetabular cup liner removal tool including features enabling removal of an acetabular liner from an acetabular cup that is implanted in a patient's acetabulum with greater efficiency and requiring fewer, easier to use tools.

SUMMARY

In accordance with one embodiment of the disclosure, there is provided a controlled force surgical implant impaction instrument including a striking assembly, a retaining pin, and an actuator component. The striking assembly is configured to deliver a controlled force impact to a surgical implant. The retaining pin is moveable between a first position and a second position. In the first position, the retaining pin inhibits distal movement of the striking assembly. In the second position, the retaining pin does not inhibit distal movement of the striking assembly. The actuator component includes a reloading channel. The actuator component is movable between a third position and a fourth position. In the third position, the retaining pin is in the first position and the retaining pin cannot be forced along the reloading channel. In the fourth position, the striking assembly can be used to move the retaining pin along the reloading channel.

In accordance with another embodiment of the disclosure, there is provided a controlled force surgical implant impaction instrument, including a rotatable actuator component, a retaining pin, and a striking assembly. The rotatable actuator component includes a reloading channel defining a reloading channel axis. The retaining pin is moveable between a first position and a second position. When the retaining pin is in the first position, the retaining pin is offset from the reloading channel axis. When the retaining pin is in the second position, the retaining pin is aligned with the reloading channel axis. The striking assembly is movable between a third position and a fourth position. When the striking assembly is in the third position and the retaining pin is in the second position, the striking assembly can be used to move the retaining pin along the reloading channel axis.

The above described features and advantages, as well as others, will become more readily apparent to those of ordinary skill in the art by reference to the following detailed description and accompanying drawings. While it would be desirable to provide a controlled force surgical implant impaction instrument that provides one or more of these or other advantageous features, the teachings disclosed herein extend to those embodiments which fall within the scope of the appended claims, regardless of whether they accomplish one or more of the above-mentioned advantages.

BRIEF DESCRIPTION OF THE DRAWINGS

Features of the controlled force surgical implant impaction instrument are apparent to those skilled in the art from the following detailed description with reference to the following drawings.

DETAILED DESCRIPTION

Figure 1:
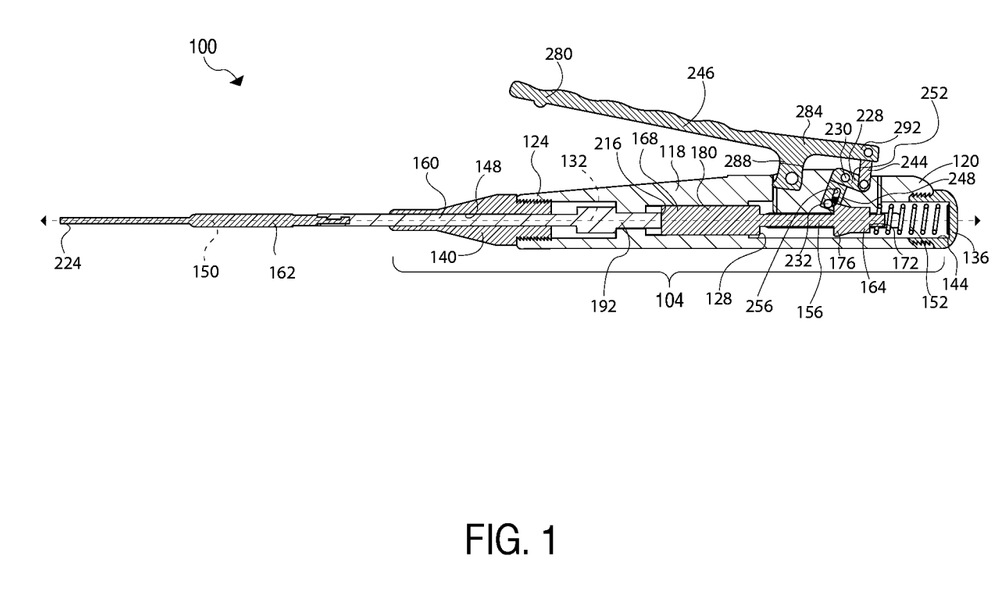
FIG. 1 depicts a side cross-sectional view of a controlled force surgical implant impaction instrument.
Figure 2:
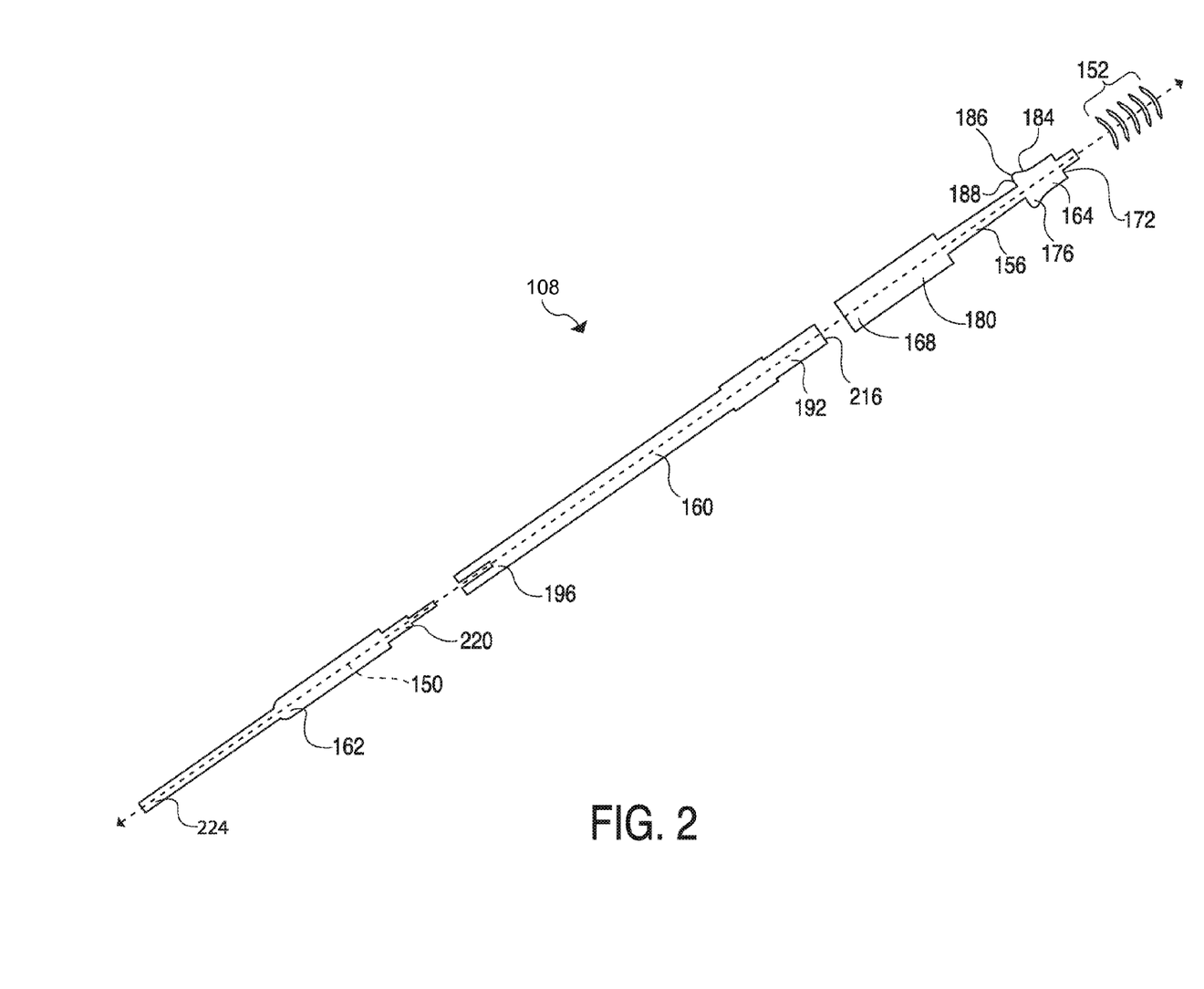
FIG. 2 depicts an exploded schematic view of the striking assembly separate from the controlled force surgical implant impaction instrument of FIG. 1.
Figure 3:
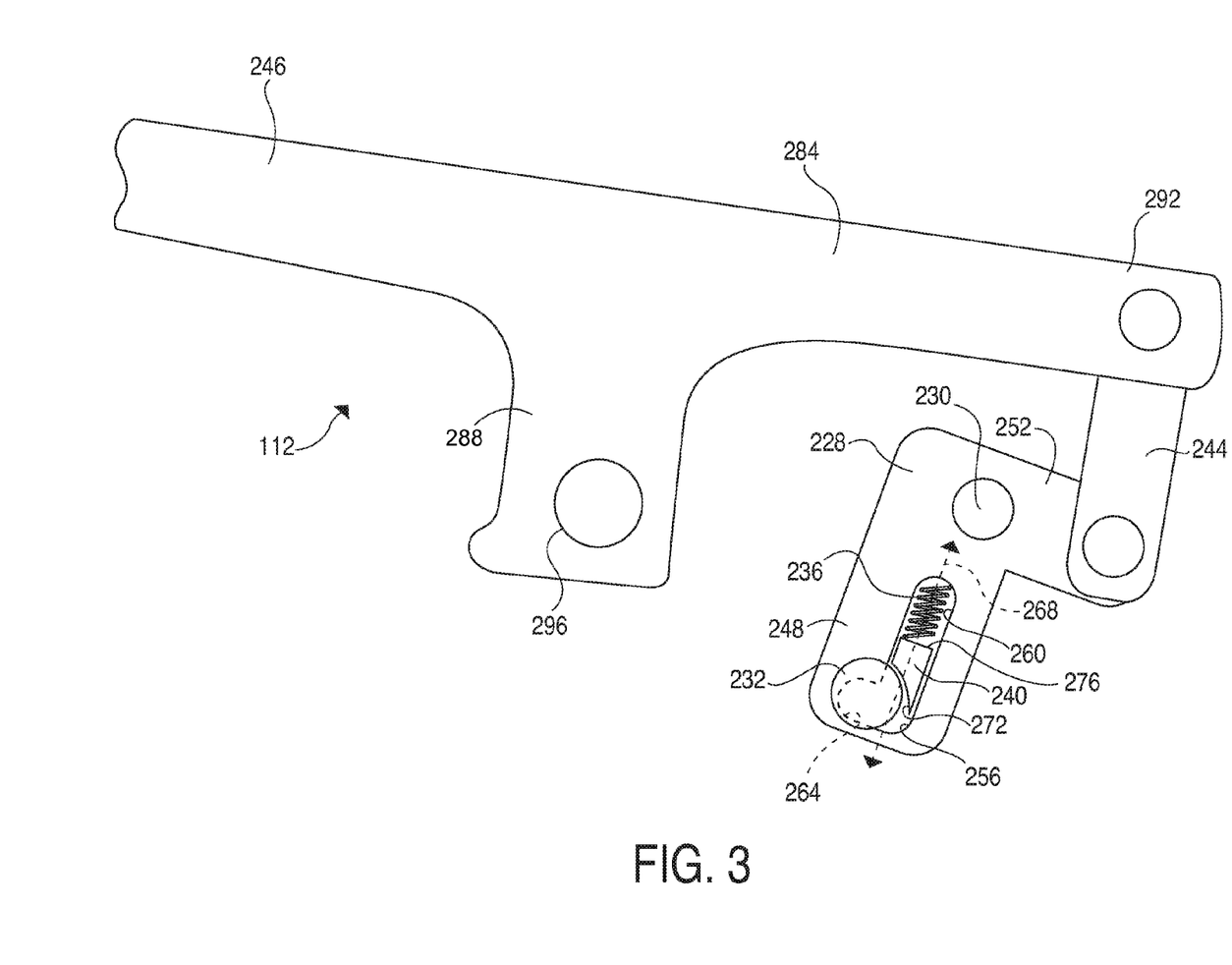
FIG. 3 depicts a side schematic view of the actuator assembly separate from the controlled force surgical implant impaction instrument of FIG. 1.

As shown in FIG. 1, the instrument 100 includes a housing assembly 104, a striking assembly 108 (shown in FIG. 2), and an actuator assembly 112 (shown in FIG. 3). The housing assembly 104 includes a housing body 118, a housing proximal end portion 120, and a housing distal end portion 124 opposite the housing proximal end portion 120. The housing assembly 104 also includes a housing assembly longitudinal opening 128 extending through the housing body 118 from the housing proximal end portion 120 to the housing distal end portion 124. The housing assembly 104 defines a housing assembly longitudinal axis 132 extending axially through the housing assembly longitudinal opening 128 through the housing proximal end portion 120 and the housing distal end portion 124. Positions and directions of features of the instrument 100 are referred to relative to the housing assembly longitudinal axis 132.

The housing assembly 104 also includes a cap 136 and a tip portion 140, each of which is aligned axially with the housing assembly longitudinal axis 132. The cap 136 is located at the housing proximal end portion 120 and is configured to threadably engage the housing body 118 at the housing proximal end portion 120. The cap 136 acts as a plug to seal the housing assembly longitudinal opening 128 at the housing proximal end portion 120. In another embodiment, the cap 136 need not threadably engage the housing proximal end portion 120, but is located at the housing proximal end portion 120 and acts as a plug to seal the housing assembly longitudinal opening 128 at the housing proximal end portion 120. The cap 136 includes a cap cavity 144 extending proximally into the cap 136 such that the cap cavity 144 extends away from the housing distal end portion 124. The housing assembly longitudinal opening 128 is adjacent to the cap cavity 144 and is in open communication with the cap cavity 144.

The tip portion 140 is located at the housing distal end portion 124 and is configured to threadably engage the housing body 118 at the housing distal end portion 124 to enable assembly/disassembly with the housing body 118 at the housing distal end portion 124. In another embodiment, the tip portion 140 need not threadably engage the housing distal end portion 124, but is located at the housing distal end portion 124 and enables assembly/disassembly with the housing body 118 at the housing distal end portion 124. The tip portion 140 defines a tip portion longitudinal opening 148 extending through the tip portion 140. The housing assembly longitudinal opening 128 is adjacent to the tip portion longitudinal opening 148 and is in open communication with the tip portion longitudinal opening 148.

As shown in FIG. 2, the striking assembly 108 includes a hammer biasing component 152, a hammer component 156, an intermediate member 160, and a contact member 162. The striking assembly 108 defines a striking assembly longitudinal axis 150 extending axially through the intermediate member 160 and the contact member 162. When the instrument 100 is assembled as shown in FIG. 1, the striking assembly 108 (shown in FIG. 2) extends through and is supported by the housing assembly 104 such that the striking assembly longitudinal axis 150 is coincident with the housing assembly longitudinal axis 132.

The hammer biasing component 152 in this embodiment is a coil spring which biases the hammer component 156 distally. In another embodiment, the hammer biasing component 152 need not be a coil spring, but is configured to bias the hammer component 156 distally. When the instrument 100 is assembled as shown in FIG. 1, the hammer biasing component 152 extends within the cap cavity 144 of the housing assembly 104.

The hammer component 156 includes a hammer component proximal end portion 164 and a hammer component distal end portion 168. The hammer component 156 further includes a hammer component biasing surface 172, a hammer component protrusion 176, and a hammer component mallet portion 180. When the instrument 100 is assembled as shown in FIG. 1, the hammer component 156, located distally relative to the hammer biasing component 152, extends within the housing assembly longitudinal opening 128 of the housing assembly 104.

The hammer component biasing surface 172 is a substantially planar surface that extends outwardly from the striking assembly longitudinal axis 150 and is located at the hammer component proximal end portion 164. The hammer component 156 is oriented such that the hammer component biasing surface 172 faces proximally and contacts the hammer biasing component 152.

The hammer component protrusion 176 also extends outwardly from striking assembly longitudinal axis 150 and is located distally relative to the hammer component biasing surface 172. The hammer component protrusion 176 includes an angled face 184, an outward-most point 186, and a flat face 188. The angled face 184 of the hammer component protrusion 176 extends outwardly and distally from the hammer component proximal end portion 164 toward the outward-most point 186. The flat face 188 of the hammer component protrusion 176 extends inwardly from the outward-most point 186. The flat face 188 is substantially parallel to the hammer component biasing surface 172 but faces in the opposite direction, or distally, toward the hammer component distal end portion 168.

The hammer component mallet portion 180 extends outwardly from the striking assembly longitudinal axis 150 such that the hammer component mallet portion 180 has a large size and, accordingly, a large mass.

The intermediate member 160 includes an intermediate member proximal end portion 192, an intermediate member distal end portion 196, and an intermediate member face 216 located at the intermediate member proximal end portion 192. The intermediate member 160 is substantially cylindrical and the intermediate member proximal end portion 192 is configured such that the intermediate member face 216 faces proximally.

The contact member 162 includes a contact member proximal end portion 220 and a contact member distal end portion 224. The contact member 162 is located distally relative to the intermediate member 160, and the contact member proximal end portion 220 is configured to couple with the intermediate member distal end portion 196 via, for example, complementary threaded portions.

When the instrument 100 is assembled as shown in FIG. 1, the intermediate member 160, located distally relative to the hammer component 156, is received within the housing assembly longitudinal opening 128 and the tip portion longitudinal opening 148 of the housing assembly 104. The intermediate member 160 extends distally of the housing assembly 104 such that the contact member 162, located distally relative to the intermediate member 160, is located entirely outside the housing assembly 104.

When the instrument 100 is assembled as shown in FIG. 1, the striking assembly 108 (shown in FIG. 2) is arranged within the housing assembly 104 such that the intermediate member 160 and the contact member 162 remain fixed relative to the housing assembly 104, but the hammer component 156 is longitudinally slidable between the housing proximal end portion 120 and the housing distal end portion 124.

Turning now to FIG. 3, the actuator assembly 112 includes an actuator component 228, a transfer member 244, and an actuator handle 246. The actuator component 228 is bent such that it is substantially L-shaped and includes a load arm 248 and a lever arm 252. In another embodiment, the actuator component 228 need not be bent such that it is substantially L-shaped, but includes a load arm 248 and a lever arm 252. The actuator component 228 is rotatably coupled to the housing body 118 at an actuator component rotation point 230 located between the load arm 248 and the lever arm 252 such that the load arm 248 and the lever arm 252 rotate together relative to the housing assembly 104.

The load arm 248 defines a reloading channel 256 extending laterally through the load arm 248. The reloading channel 256 is substantially L-shaped having a reloading portion 260 and a retaining portion 264 in open communication with one another. The reloading portion 260 of the reloading channel 256 defines a reloading channel axis 268. The reloading channel axis 268 extends through the reloading portion 260 of the reloading channel 256 but does not extend through the retaining portion 264 of the reloading channel 256. The lever arm 252 is rotatably coupled to the transfer member 244.

Figure 4:
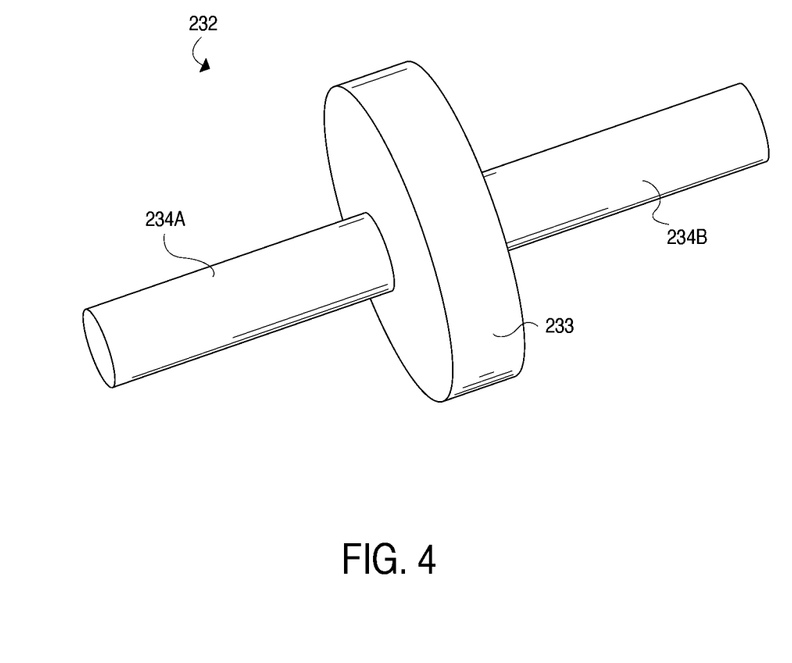
FIG. 4 depicts a side perspective schematic view of the retaining pin of the actuator assembly of FIG. 3.

The actuator assembly 112 further includes a retaining pin 232, a retaining pin biasing member 236, and a ramp member 240 all disposed within the reloading channel 256 of the load arm 248 of the actuator component 228. For clarity, the retaining pin 232 is shown in more detail in FIG. 4 separated from the rest of the actuator assembly 112. The retaining pin 232 includes a central portion 233 and post portions 234A and 234B arranged on opposite ends of the central portion 233. The central portion 233 is sized and configured to extend within the reloading channel 256 (shown in FIG. 3) such that when the retaining pin 232 is positioned within the reloading channel 256, the post portions 234A and 234B (shown in FIG. 4) are positioned on either side of the actuator component 228 (shown in FIG. 3). The actuator assembly 112 (shown in FIG. 3) is arranged relative to the housing assembly 104 (shown in FIG. 1) and the striking assembly 108 (shown in FIG. 2) such that the central portion 233 of the retaining pin 232 (shown in FIG. 4) is in contact with the hammer component protrusion 176.

Returning to FIG. 3, the actuator assembly 112 is configured such that the retaining pin 232 is movable within the reloading channel 256 by sliding between the retaining portion 264 and the reloading portion 260 of the reloading channel 256. Additionally, the actuator assembly 112 is configured such that the retaining pin 232 is movable relative to the housing assembly 104 because the retaining pin 232 is retained within the actuator component 228 which is rotatably coupled to the housing body 118 at the actuator component rotation point 230.

Continuing with FIG. 3, the ramp member 240 is positioned within the reloading portion 260 of the reloading channel 256 adjacent to the retaining pin 232. The ramp member 240 includes a ramp portion 272, configured to contact the central portion 233 of the retaining pin 232 (shown in FIG. 4), and a cylindrical portion 276, opposite the ramp portion 272, configured to contact the retaining pin biasing member 236. The ramp portion 272 is angled such that the ramp member 240 generally faces toward the retaining portion 264 of the reloading channel 256. Accordingly, the ramp portion 272 of the ramp member 240 generally biases the retaining pin 232 toward the retaining portion 264 of the reloading channel 256.

The retaining pin biasing member 236 is mounted within the reloading portion 260 of the reloading channel 256 and is operably coupled to the ramp member 240. The retaining pin biasing member 236 is configured to bias the ramp member 240 toward the retaining pin 232 such that the ramp member 240 in turn biases the retaining pin 232 toward the retaining portion 264 of the reloading channel 256. The retaining pin biasing member 236 is a coil spring oriented along the reloading channel axis 268. In another embodiment, the retaining pin biasing member 236 need not be a coil spring, but is oriented along the reloading channel axis 268 and biases the ramp member 240 toward the retaining pin 232.

The actuator handle 246 includes an actuator handle free end portion 280 (shown in FIG. 1) and an actuator handle coupled end portion 284. When the instrument 100 is assembled as shown in FIG. 1, the actuator handle coupled end portion 284 is coupled to the housing body 118 of the housing assembly 104 and the actuator handle free end portion 280 extends away from the housing assembly 104 such that the actuator handle 246 generally extends along the housing assembly 104. The actuator handle 246 is elongated and is substantially planar such that it acts as the beam portion of a lever.

The actuator handle coupled end portion 284 includes an actuator handle rotating portion 288 rotatably coupled to the housing body 118 as shown in FIG. 1. The actuator handle coupled end portion 284 further includes an actuator handle actuating portion 292 rotatably coupled to the transfer member 244. The actuator handle rotating portion 288 extends inwardly from the actuator handle 246 such that the actuator handle 246 acts as the beam portion and the actuator handle rotating portion 288 acts as a fulcrum portion of a lever.

The actuator handle 246 further includes an actuator handle biasing member 296 configured to bias the actuator handle free end portion 280 away from the housing assembly longitudinal axis 132 (shown in FIG. 1). The actuator handle biasing member 296 is a torsion spring located within the actuator handle rotating portion 288. In another embodiment, the actuator handle biasing member 296 need not be a torsion spring, but is located within the actuator handle rotating portion 288 and is configured to bias the actuator handle free end portion 280 away from the housing assembly longitudinal axis 132 (shown in FIG. 1).

In operation, the controlled force surgical implant impaction instrument 100 is operated to deliver a controlled force impact to a surgical implant. In this embodiment, the instrument 100 delivers a controlled force impact to an acetabular cup thereby loosening a liner from the acetabular cup for removal. In alternative embodiments, the instrument 100 is operated to deliver a controlled force impact to other surgical implants during surgical procedures. By way of example, in an alternative embodiment, the instrument 100 is operated to deliver a controlled force impact to an acetabular cup liner to secure the liner within the acetabular cup. In another alternative embodiment, the instrument 100 is operated to deliver a controlled force impact to a femoral head to secure the femoral head on a hip stem with a taper fit. In another alternative embodiment, the instrument 100 is operated to deliver a controlled force impact to a Steinmann pin to secure the pin for skeletal traction. In another alternative embodiment, the instrument 100 is operated to deliver a controlled force impact to a portion of a modular stem to secure the portions of the stem to one another with a taper fit.

In the resting configuration, shown in FIG. 1, wherein no external force is applied to the instrument 100, the hammer biasing component 152 biases the hammer component 156 distally against the intermediate member 160, and the actuator handle biasing member 296 (shown in FIG. 3) biases the actuator handle 246 clockwise about the actuator handle rotating portion 288.

Due to the lever configuration of the actuator handle 246, when the actuator handle 246 is biased clockwise, the actuator handle free end portion 280 is positioned away from the housing body 118 and the actuator handle coupled end portion 284, and specifically the actuator handle actuating portion 292, is positioned near the housing body 118. Because the transfer member 244 is rotatably coupled to the actuator handle actuating portion 292, the transfer member 244 is therefore forced inwardly toward the housing assembly longitudinal axis 132. Because the transfer member 244 is also rotatably coupled to the lever arm 252 of the actuator component 228, when the transfer member 244 is forced inwardly, the actuator component 228 is rotated clockwise about the actuator component rotation point 230. Because the retaining pin 232 is arranged within the load arm 248 of the actuator component 228, when the actuator component 228 is rotated clockwise, the retaining pin 232 is positioned against the flat face 188 of the hammer component protrusion 176.

Because the actuator assembly 112 (shown in FIG. 3) is configured such that the retaining pin 232 is in contact with the hammer component protrusion 176, the rotational position of the actuator component 228 relative to the housing assembly 104 determines the position of the retaining pin 232 relative to the hammer component protrusion 176 and, thus, also determines the position of the hammer component 156 relative to the housing assembly 104 (shown in FIG. 1).

More specifically, when the instrument 100 is in the resting configuration, the load arm 248 is angled inwardly and distally and the retaining pin 232 is in the retaining portion 264 of the reloading channel 256 (shown in FIG. 3) and rests on the flat face 188 of the hammer component protrusion 176. When the retaining pin 232 is in the retaining portion 264 of the reloading channel 256, the retaining pin 232 is offset from the reloading channel axis 268 (shown in FIG. 3). When the retaining pin 232 rests on the flat face 188 of the hammer component protrusion 176, the retaining pin biasing member 236 is unconstrained and biases the ramp member 240 (shown in FIG. 3) inwardly. The ramp member 240, in turn, biases the retaining pin 232 inwardly and distally. Because the retaining pin 232 is biased inwardly and distally, the retaining pin 232 applies no force to the flat face 188 of the hammer component protrusion 176. Accordingly, the hammer biasing component 152 is unconstrained and biases the hammer component 156 distally within the housing assembly 104.

Figure 5:
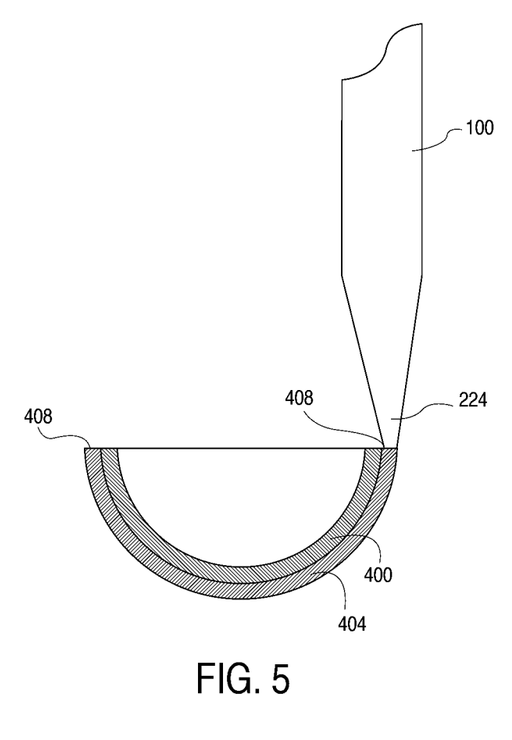
FIG. 5 depicts a side schematic view of a distal portion of the controlled force surgical implant impaction instrument of FIG. 1 in use.

When ready to use the instrument 100, the physician places the contact member distal end portion 224 in contact with the surgical implant to be impacted. In this embodiment, the physician places the contact member distal end portion 224 in contact with an outer edge 408 of the acetabular cup 404 as shown in FIG. 5. For clarity, the acetabular cup 404 and liner 400 are shown in a cross-sectional view in FIG. 5. When the physician initially places the controlled force surgical implant impaction instrument 100 in contact with the outer edge 408 of the acetabular cup 404, the controlled force surgical implant impaction instrument 100 is arranged in the resting configuration, as shown in FIG. 6.

Figure 6:
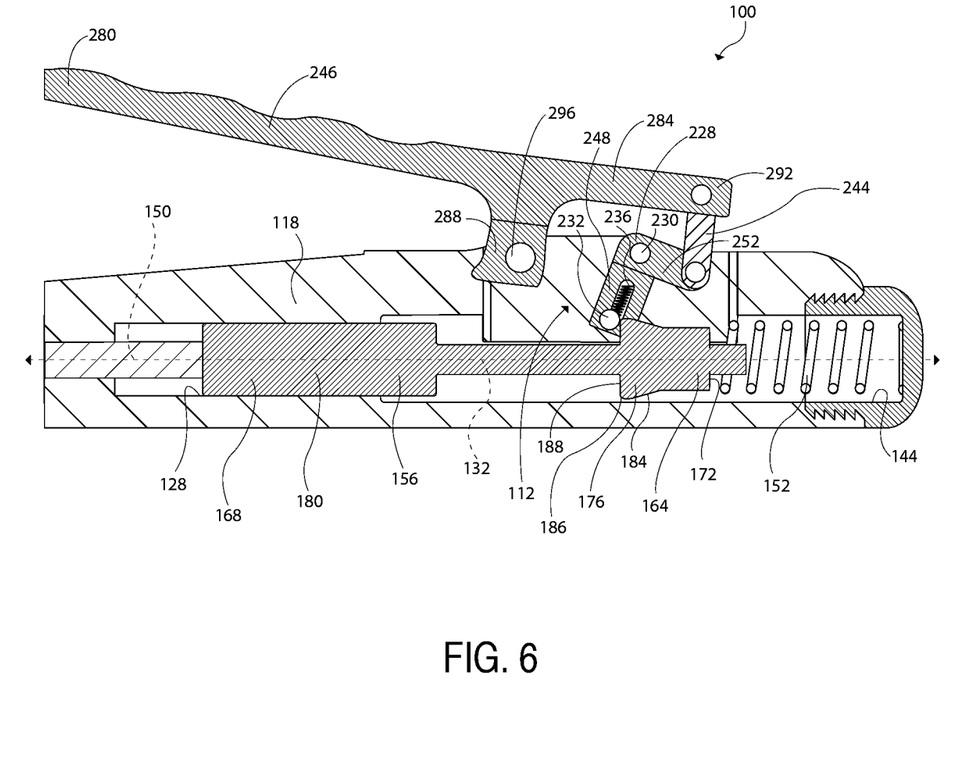
FIG. 6 depicts a cross-sectional view of a portion of the controlled force surgical implant impaction instrument of FIG. 1 when the instrument is arranged in the resting configuration.
Figure 7:
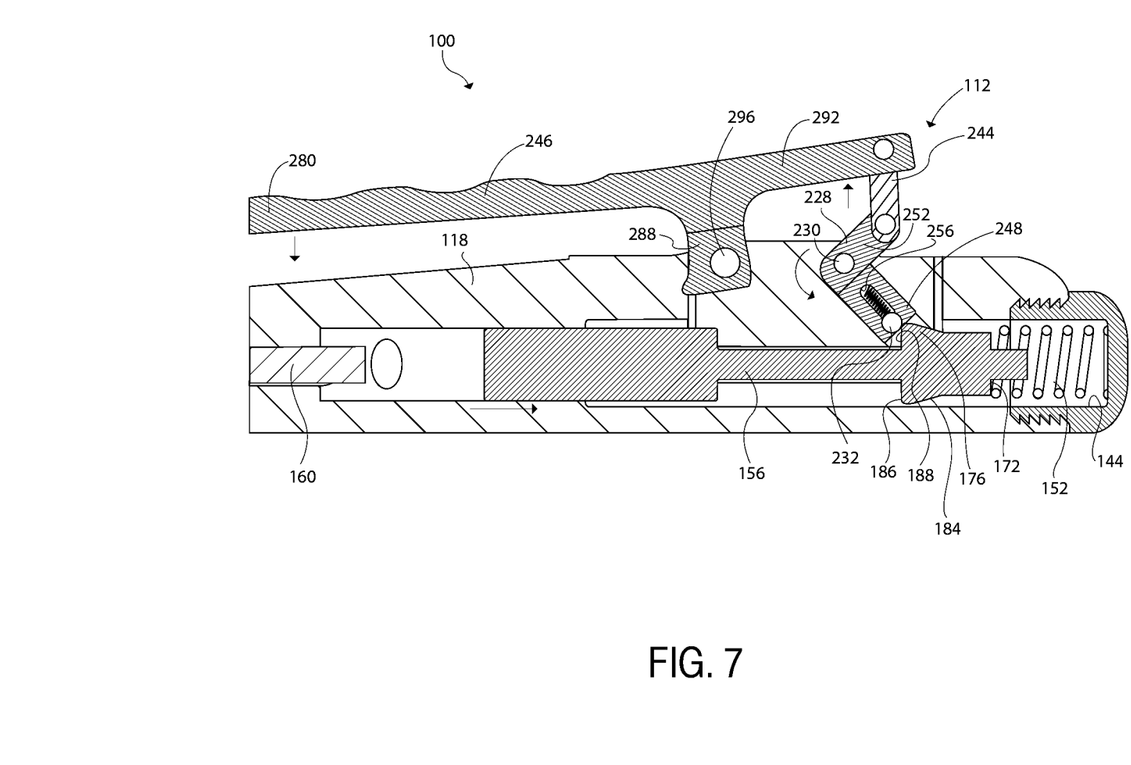
FIG. 7 depicts a side cross-sectional view of a portion of the controlled force surgical implant impaction instrument of FIG. 1 arranged in the loaded configuration.

When ready to apply the impact to the surgical implant, the physician grips both the housing assembly 104 and the actuator handle 246 of the instrument 100 as shown in FIGS. 1 and 6 in one hand and squeezes inwardly toward the striking assembly longitudinal axis 150 to apply force to the actuator handle 246 toward the housing body 118. When the physician applies initial inward force to squeeze the actuator handle free end portion 280 toward the housing assembly 104, the controlled force surgical implant impaction instrument 100 moves from the resting configuration (shown in FIGS. 1 and 6) toward the loaded configuration which is shown in FIG. 7.

More specifically, the physician squeezes the actuator handle free end portion 280 with enough force to overcome the force of the actuator handle biasing member 296 in the actuator handle rotating portion 288 and compresses the actuator handle biasing member 296 such that energy is stored in the actuator handle biasing member 296.

Pressing the actuator handle free end portion 280 toward the housing body 118, rotates the actuator handle 246 about the actuator handle rotating portion 288 and moves the actuator handle actuating portion 292 away from the housing body 118. Moving the actuator handle actuating portion 292 away from the housing body 118 pulls the transfer member 244 of the actuator assembly 112 outwardly. Because the transfer member 244 is rotatably coupled to the lever arm 252 of the actuator component 228, pulling the transfer member 244 outwardly rotates the actuator component 228 counter-clockwise about the actuator component rotation point 230 such that the load arm 248 also rotates counter-clockwise about the actuator component rotation point 230. Because the retaining pin 232 is positioned within retaining portion 264 of the reloading channel 256 of the load arm 248, rotating the load arm 248 of the actuator component 228 counter-clockwise in turn rotates the retaining pin 232 counter-clockwise about the actuator component rotation point 230.

Rotating the retaining pin 232 counter-clockwise about the actuator component rotation point 230 causes the retaining pin 232 to apply force to the flat face 188 of the hammer component protrusion 176 which moves the hammer component 156 proximally. The retaining pin 232 thereby inhibits distal movement of the hammer component 156.

The physician initially squeezes the actuator handle free end portion 280 with enough force such that the retaining pin 232 overcomes the force of the hammer biasing component 152. By overcoming the force of the hammer biasing component 152, the retaining pin 232 moves the hammer component 156 proximally within the housing assembly 104 (shown in FIG. 1). As the hammer component 156 moves proximally, the hammer component 156 becomes spaced apart from the intermediate member 160 which is fixed relative to the housing assembly 104 (shown in FIG. 1). Additionally, as the hammer component 156 moves proximally, the hammer component biasing surface 172 compresses the hammer biasing component 152 within the cap cavity 144 such that energy is stored in the hammer biasing component 152.

Squeezing the actuator handle free portion 280 closer toward the housing assembly longitudinal axis 132 causes further counter-clockwise rotation of the actuator handle 246 about the actuator handle rotating portion 288. Further counter-clockwise rotation of the actuator handle 246 causes the retaining pin 232 to continue to rotate counter-clockwise about the actuator component rotation point 230. Further counter-clockwise rotation of the retaining pin 232 causes the retaining pin 232 to travel along the flat face 188 of the hammer component protrusion 176 and to further apply force to the flat face 188 in the proximal direction. Once the retaining pin 232 has rotated about the actuator component rotation point 230 such that it is positioned at the outward-most point 186 of the hammer component protrusion 176, the retaining pin 232 slips past the outward-most point 186 and slips onto the angled face 184 of the hammer component protrusion 176.

As noted above, the retaining pin biasing member 236 and ramp member 240 bias the retaining pin 232 inwardly and distally toward the retaining portion 264 of the reloading channel 256. Additionally, counter-clockwise rotation of the retaining pin 232 about the actuator component rotation point 230 forces the retaining pin 232 against the flat face 188 and the outward-most point 186 of the hammer component protrusion 176, thereby applying a distal force to the retaining pin 232. Accordingly, as the retaining pin 232 travels along the flat face 188 and past the outward-most point 186, the hammer component protrusion 176 cannot force the retaining pin 232 to move from the retaining portion 264 to the reloading portion 260 within the reloading channel 256.

Figure 8:
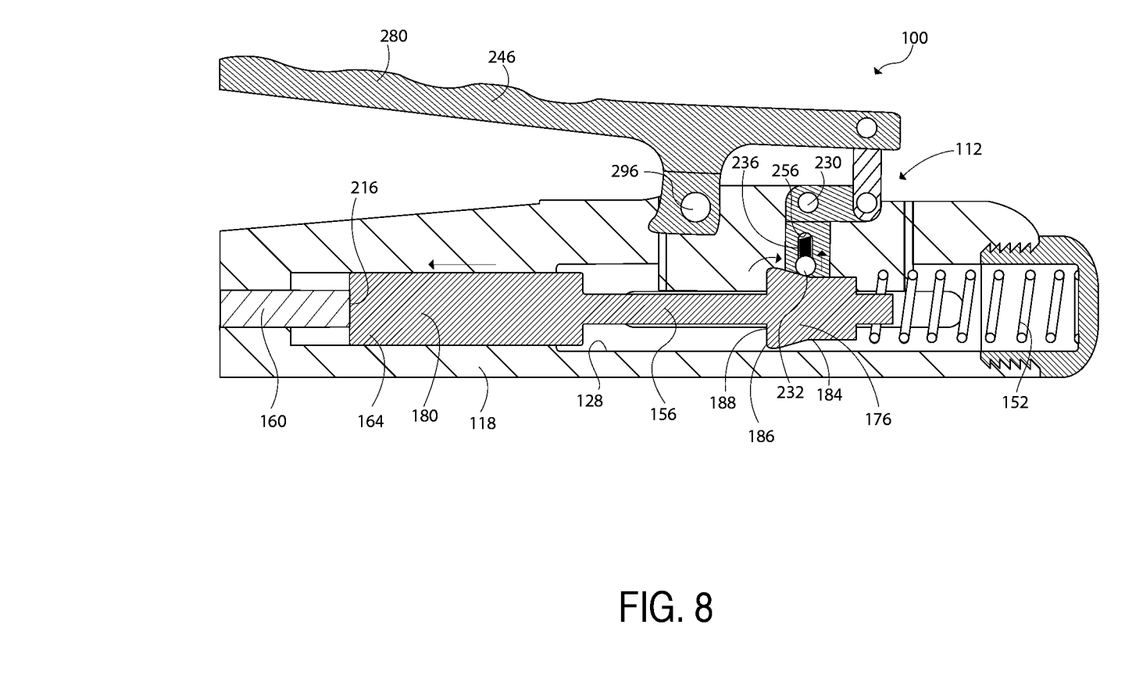
FIG. 8 depicts a side cross-sectional view of a portion of the controlled force surgical implant impaction instrument of FIG. 1 arranged in the actuated configuration.

As shown in FIG. 8, wherein the instrument 100 is arranged in the actuated configuration, the retaining pin 232 is in contact with the angled face 184 of the hammer component protrusion 176. Once the instrument 100 is in the actuated position, the retaining pin 232 no longer applies proximal force to the hammer component 156. In other words, the retaining pin 232 no longer inhibits distal movement of the hammer component 156. The hammer component 156 is free to slide distally and no longer constrains the hammer biasing component 152. Accordingly, the hammer component 156 slides distally within the housing assembly 104 due to the force applied by the release of the stored energy of the hammer biasing component 152.

The hammer component 156 slides distally within the housing assembly 104 (shown in FIG. 1) toward the intermediate member 160 until the hammer component proximal end portion 164 on the hammer component mallet portion 180 contacts intermediate member face 216 on the intermediate member 160. Accordingly, the striking assembly 108 is configured such that when the hammer component 156 slides distally within the housing assembly longitudinal opening 128, the relatively large mass of the hammer component mallet portion 180 is able to impart force to the intermediate member face 216 upon contact between the movable hammer component distal end portion 168 and the fixed intermediate member proximal end portion 192.

Upon contact of the hammer component mallet portion 180 with the intermediate member 160, the hammer component 156 transfers the distal force to the intermediate member 160. The distal force then propagates distally through the intermediate member 160 and into the contact member 162 (shown in FIG. 1). The distal force propagates through the contact member 162 to the contact member distal end portion 224 (shown in FIG. 1) and thereby impacts the surgical implant. In this case, distal force impacts the outer edge 408 of the acetabular cup 404 (shown in FIG. 5). In alternative embodiments, the contact member distal end portion 224 is configured with a tip having a size and shape suited to deliver an impact to a particular surgical implant. By way of example, in one embodiment, the contact member distal end portion 224 is configured with a tip having a size and shape suited to impacting an acetabular cup liner to secure the liner within an acetabular cup. In another embodiment, the contact member distal end portion 224 is configured with a tip having a size and shape suited to impacting a femoral head to secure the femoral head on a hip stem with a taper fit. In another embodiment, the contact member distal end portion 224 is configured with a tip having a size and shape suited to impacting a Steinmann pin to secure the pin for skeletal traction. In another embodiment, the contact member distal end portion 224 is configured with a tip having a size and shape suited to impacting a portion of a modular stem to secure the portions of the stem to one another with a taper fit.

Because the distal force that propagates through the striking assembly 108 (shown in FIG. 1) to the outer edge 408 of the acetabular cup 404 (shown in FIG. 5) is generated by the hammer biasing component 152, the amount of distal force applied to the acetabular cup 404 by the contact member distal end portion 224 (shown in FIG. 5) is consistent each time the controlled force surgical implant impaction instrument 100 is operated.

Once the physician has delivered the distal force to the surgical implant, in this case the outer edge 408 of the acetabular cup 404, the physician is able to subsequently deliver another distal force to the outer edge 408 of the acetabular cup 404 without removing the controlled force surgical implant impaction instrument 100 from contact with the outer edge 408 of the acetabular cup 404 (shown in FIG. 5). To do so, the physician relaxes the grip on the actuator handle free end portion 280 such that the inward force no longer overcomes the force of the actuator handle biasing member 296, the hammer biasing component 152, and the retaining pin biasing member 236. When no external force is applied to the controlled force surgical implant impaction instrument 100, the instrument 100 then automatically returns to the resting position shown in FIGS. 1 and 6.

The actuator handle biasing member 296 rotates the actuator handle 246 clockwise about the actuator handle rotating portion 288 due to the force applied by the release of the stored energy of the actuator handle biasing member 296. Rotating the actuator handle 246 clockwise forces the transfer member 244 inwardly via the actuator handle coupled end portion 284. When the transfer member 244 is forced inwardly, the actuator component 228 is rotated clockwise about the actuator component rotation point 230. As the load arm 248 of the actuator component 228 is rotated clockwise, the retaining pin 232 is forced against the angled face 184 of the hammer component protrusion 176. Because the angled face 184 is oriented in the opposite direction as the ramp member 240 (shown in FIG. 3), the angled face 184 biases the retaining pin 232 proximally within the reloading channel 256. The force applied by the actuator handle biasing member 296 is strong enough to overcome the force applied by the retaining pin biasing member 236 such that the retaining pin biasing member 236 is compressed within the reloading portion 260 of the reloading channel 256 and energy is stored within the retaining pin biasing member 236.

When the retaining pin biasing member 236 is compressed within the reloading portion 260 of the reloading channel 256 and the angled face 184 biases the retaining pin 232 proximally, the retaining pin 232 moves from the retaining portion 264 to the reloading portion 260 of the reloading channel 256. When the retaining pin 232 is in the reloading portion 260, the retaining pin 232 is aligned with the reloading channel axis 268 (shown in FIG. 3). Thus, the angled face 184 of the hammer component protrusion 176 of the hammer component 156 forces the retaining pin 232 into alignment with the reloading channel axis 268 (shown in FIG. 3).

While the retaining pin 232 is positioned within the reloading portion 260 of the reloading channel 256 (shown in FIG. 3), the actuator component 228 continues to rotate clockwise about the actuator component rotation point 230. Thus, the retaining pin 232 also continues to rotate clockwise about the actuator component rotation point 230 and thereby travels distally along the angled face 184 of the hammer component protrusion 176. Once the retaining pin 232 slips distally past the outward-most point 186 of the hammer component protrusion 176 and back to the flat face 188 of the hammer component protrusion 176, the force applied by the release of the stored energy of the retaining pin biasing member 236 forces the retaining pin 232 inwardly.

Because the ramp portion 272 biases the retaining pin 232 inwardly and distally and the retaining pin biasing member 236 biases the ramp member 240 inwardly, the retaining pin 232 moves within the reloading channel 256 from the reloading portion 260 back to the retaining portion 264 (shown in FIG. 3). When the retaining pin 232 returns to the retaining portion 264 of the reloading channel 256, the controlled force surgical implant impaction instrument 100 is again arranged in the resting configuration.

In another embodiment, the amount of distal force applied to the surgical implant, by the contact member distal end portion 224 is varied by replacing the hammer biasing component 152. The replacement hammer biasing component has a different spring constant and, therefore, applies a different amount of distal force when releasing stored energy. The replacement hammer biasing component is configured to deliver an impact having a force suited for a particular use. By way of example, in one embodiment, the replacement hammer biasing component is configured to deliver an impact having a force suited to securing an acetabular cup liner within an acetabular cup. In another embodiment, the replacement hammer biasing component is configured to deliver an impact having a force suited to securing a femoral head on a hip stem with a taper fit. In another embodiment, the replacement hammer biasing component is configured to deliver an impact having a force suited to securing a Steinmann pin for skeletal traction. In another embodiment, the replacement hammer biasing component is configured to deliver an impact having a force suited to securing portions of a modular stem to one another with a taper fit.

The hammer biasing component can be replaced easily by disengaging the cap 136 from the housing body 118 at the housing proximal end portion 120. Because the hammer biasing component extends within the cap cavity 144, once the cap 136 is removed from the housing body 118, the replacement hammer biasing component can be installed and the cap 136 can then be reengaged with the housing body 118.

The foregoing detailed description of one or more embodiments of the controlled force surgical implant impaction instrument has been presented herein by way of example. It will be recognized that there are advantages to certain individual features and functions described herein that may be obtained without incorporating other features and functions described herein. Moreover, it will be recognized that various alternatives, modifications, variations or improvements of the above-disclosed embodiments and other features and functions, or alternatives thereof, may be desirably combined into many other different embodiments, systems or applications. Presently unforeseen or unanticipated alternatives, modifications, variations or improvements therein may be subsequently made by those skilled in the art which are also intended to be encompassed by the appended claims. Therefore, the spirit and scope of any appended claims should not be limited to the description of the embodiments contained herein.

What is claimed is:

1. A controlled force surgical implant impaction instrument, comprising:
   a striking assembly configured to impact a surgical implant;
   a retaining pin moveable between a first position whereat the retaining pin inhibits distal movement of the striking assembly, and a second position whereat the retaining pin does not inhibit distal movement of the striking assembly; and
   an actuator component including a reloading channel, the actuator component movable between (i) a third position whereat the retaining pin is in the first position and the retaining pin cannot be forced within the reloading channel, and (ii) a fourth position whereat the striking assembly can be used to move the retaining pin within the reloading channel.

2. The controlled force surgical implant impaction instrument of claim 1, wherein the actuator component is rotatable between the third position and the fourth position.

3. The controlled force surgical implant impaction instrument of claim 1, further comprising:
  a housing assembly supporting the striking assembly; and
  an actuator handle operably connected to the actuator component, the actuator handle extending along the housing assembly.

4. The controlled force surgical implant impaction instrument of claim 3, wherein the actuator handle is rotatably connected to the housing assembly.

5. The controlled force surgical implant impaction instrument of claim 4, wherein:
  the striking assembly defines a striking axis; and
  the actuator handle is rotatable toward and away from the striking axis.

6. The controlled force surgical implant impaction instrument of claim 4, wherein the actuator component is rotatably connected to the housing assembly.

7. The controlled force surgical implant impaction instrument of claim 6, further comprising:
  a transfer member rotatably connected to the actuator handle and rotatably connected to the actuator component.

8. The controlled force surgical implant impaction instrument of claim 7, wherein the actuator component further comprises:
  a lever arm; and
  a load arm, wherein the transfer member is rotatably connected to the lever arm, the load arm defines the reloading channel.

9. The controlled force surgical implant impaction instrument of claim 1, further comprising:
  a biasing member configured to bias the retaining pin toward the first position.

10. The controlled force surgical implant impaction instrument of claim 1, further comprising:
  a ramp member operably connected to the biasing member and to the retaining pin, wherein the ramp member and the biasing member are configured to bias the retaining pin toward the first position.

11. The controlled force surgical implant impaction instrument of claim 10, wherein the first position is offset from the reloading channel.

12. A controlled force surgical implant impaction instrument, comprising:
  a rotatable actuator component including a reloading channel defining a reloading channel axis;
  a retaining pin moveable between a first position whereat the retaining pin is offset from the reloading channel axis, and a second position whereat the retaining pin is aligned with the reloading channel axis; and
  a striking assembly movable between a third position and a fourth position, the striking assembly configured such that when the striking assembly is in the third position and the retaining pin is in the second position, the striking assembly can be used to move the retaining pin along the reloading channel axis.

13. The controlled force surgical implant impaction instrument of claim 12, further comprising:
  a housing assembly supporting the striking assembly; and
  an actuator handle operably connected to the actuator component, the actuator handle extending along the housing assembly.

14. The controlled force surgical implant impaction instrument of claim 13, wherein the actuator handle is rotatably connected to the housing assembly.

15. The controlled force surgical implant impaction instrument of claim 14, wherein:
  the striking assembly defines a striking axis; and
  the actuator handle is rotatable toward and away from the striking axis.

16. The controlled force surgical implant impaction instrument of claim 12, further comprising:
  a first biasing member configured to bias the retaining pin toward the first position.

17. The controlled force surgical implant impaction instrument of claim 16, further comprising:
  a second biasing member configured to bias the actuator handle, the controlled force surgical implant impaction instrument configured such that the retaining pin is forced to the first position when no external force is applied to the controlled force surgical implant impaction instrument.

18. The controlled force surgical implant impaction instrument of claim 14, wherein the actuator component is rotatably connected to the housing assembly.

19. The controlled force surgical implant impaction instrument of claim 16, further comprising:
  a transfer member rotatably connected to the handle and rotatably connected to the actuator component.

20. The controlled force surgical implant impaction instrument of claim 17, wherein the actuator component further comprises:
  a lever arm; and
  a load arm, wherein the transfer member is rotatably connected to the lever arm, the load arm defines the reloading channel.

* * * * *